United States Patent [19]

Turcott

[11] Patent Number: 5,645,070

[45] Date of Patent: Jul. 8, 1997

[54] METHOD AND APPARATUS FOR DETERMINING THE ORIGINS OF CARDIAC ARRHYTHMIAS MORPHOLOGY DYNAMICS

[75] Inventor: Robert Turcott, Redwood City, Calif.

[73] Assignee: Ventritex, Inc., Sunnyvale, Calif.

[21] Appl. No.: 533,300

[22] Filed: Sep. 25, 1995

[51] Int. Cl.⁶ .................................................. A61B 5/04
[52] U.S. Cl. ............................................................ 128/702
[58] Field of Search ........................ 128/889, 702–705; 364/413.05, 413.06

[56] References Cited

U.S. PATENT DOCUMENTS

| | | | |
|---|---|---|---|
| 4,587,976 | 5/1986 | Schmid et al. | 128/699 |
| 4,732,157 | 3/1988 | Kaplan et al. | 128/696 |
| 4,893,632 | 1/1990 | Armington | 128/696 |
| 4,922,920 | 5/1990 | Thie et al. | 128/699 |
| 5,148,812 | 9/1992 | Verrier et al. | 128/704 |
| 5,201,321 | 4/1993 | Fulton | 128/702 |
| 5,280,792 | 1/1994 | Leong et al. | 128/702 |
| 5,366,487 | 11/1994 | Adams et al. | 128/705 |
| 5,404,880 | 4/1995 | Throne | 128/705 |
| 5,439,004 | 8/1995 | Duong-van et al. | 128/705 |
| 5,447,519 | 9/1995 | Peterson | 607/5 |
| 5,453,940 | 9/1995 | Broomhead et al. | 364/553 |

OTHER PUBLICATIONS

"Is Fibrillation Chaos?", Kaplan, et al., Circulation Research, vol. 67, No. 4, Oct. 1990, pp. 886–892.

"Lack of Evidence for Low–Dimensional Chaos in Heart Rate Variablity", Kanters, et al., Nonlinear Dynamics in Heart Rate, pp. 591–601.

*Primary Examiner*—William E. Kamm
*Attorney, Agent, or Firm*—Steven M. Mitchell; Mark J. Meltzer

[57] ABSTRACT

A method of discriminating among cardiac rhythms of supraventricular and ventricular origin by exploiting the differences in their underlying dynamics reflected in the morphology of the waveform. A phase space representation of the dynamics of a waveform is obtained from the electrogram signal amplitude by using the technique of delay embedding. A first cardiac rhythm electrogram of known origin is sensed and a phase space representation or trajectory is generated for use as a template. A second or test cardiac rhythm electrogram is sensed and a phase space representation is generated from the detected waveform complex. This second phase space representation is compared to the template to distinguish between the origins of the first and second cardiac rhythms. If a test trajectory is sufficiently different from the template trajectory, the test complex is deemed to have different dynamics, and therefore be from a different origin than the template.

23 Claims, 6 Drawing Sheets

SIMPLE OSCILLATOR

DAMPED OSCILLATOR 5,645,070

METHOD AND APPARATUS FOR DETERMINING THE ORIGINS OF CARDIAC ARRHYTHMIAS MORPHOLOGY DYNAMICS

FIELD OF THE INVENTION

The present invention relates generally to heart monitors, implantable defibrillators and pacemakers and more particularly to a method and apparatus for discriminating among cardiac arrhythmias.

BACKGROUND OF THE INVENTION

The ability of tiered-therapy implantable cardioverter defibrillators (ICDs) to deliver appropriate therapy depends in part on their ability to discriminate among various cardiac arrhythmias. The primary parameter used for discrimination has been heart rate. Other characteristics of electrograms which have been used are suddenness of onset of a high rate, rate stability, and morphology of the QRS complex. The limited computational capacity of contemporary devices has, for morphology-based discriminators, led developers to focus on techniques that rely on rather superficial properties of the electrogram. It is desirable to develop an algorithm which operates on the fundamental properties of the electrogram, but is not computationally intensive.

An arrhythmia of ventricular origin is conducted throughout the ventricles by a different path than the specialized conduction system which conveys supraventricular rhythms. As used herein, supraventricular rhythms include both normal rhythms such as sinus rhythm as well as arrhythmias of supraventricular origin such as atrial fibrillation. The different pathways used by ventricular and supraventricular rhythms have different dynamics, which give rise to differences in morphology between these two classes of rhythms. It would be beneficial to have an arrhythmia discrimination algorithm which treats electrograms as having arisen from a dynamical system.

A dynamical system is a system that can be described by a set of coupled differential equations. The degrees of freedom, m, of the system is the number of variables needed to characterize the system's behavior, or equivalently, the number of equations in the set of coupled, first-order differential equations. A phase space is a mathematical m-dimensional space where each dimension is associated with one of the m system variables. Since the state of the system at a particular time is given by the value of each variable, the state can be represented by the location of a point in the phase space. As the system evolves with time, the value of each variable changes, and the point characterizing the state of the system moves in the space. The time-evolution of the system is thus characterized by the trajectory of the point in phase space. The trajectory is determined by the differential equations governing the system, so the phase space representation embodies the dynamical properties of the equations.

In analyzing experimental data, one typically has access to a single variable, such as position, rather than the entire set of m state variables. One of the profound insights that has arisen from chaos theory is the recognition that a topologically equivalent representation of phase space can be constructed from the observation of a single variable. Access to all the state variables is therefore unnecessary.

It is reasonable to view the voltage recorded by an electrogram as arising from a dynamical system. Different systems are responsible for propagation through the myocardium and the specialized conducting system. Differences between the trajectories of rhythms of ventricular and supraventricular origin should then be apparent in the reconstructed phase space. An algorithm based on this approach is thus more than just an empirical technique: it relies on the differences in the fundamental dynamics of the system, the same information given by the differential equations that model the system. However, since our interest is in discrimination, and not in identifying the intrinsic properties of the putative dynamical systems, the necessary degree of rigor is greatly relaxed. For example, it is not necessary to determine the true dimensionality of the system or address issues of noise; it is sufficient to simply extract enough of the dynamical differences that the systems can be distinguished.

It is therefore an object of the present invention to provide a method and apparatus for distinguishing between cardiac rhythms of supraventricular and ventricular origins.

It is a further object of the invention to provide a computationally efficient method for using depolarization morphology for distinguishing cardiac rhythms.

SUMMARY OF THE INVENTION

The present invention exploits the differences in the underlying dynamical properties of cardiac arrhythmias as manifest by electrogram morphology, while avoiding computationally intensive processing during routine use. More particularly, a method of discriminating cardiac arrhythmias by exploiting the differences in their underlying dynamics reflected in the morphology of the waveform is provided. A mathematical representation of the dynamics of a waveform is obtained from a single measurable variable, particularly electrogram signal amplitude in the preferred embodiment, by using the technique of delay embedding. This representation, which is a trajectory in an abstract space, is topologically equivalent to the attractor that describes the system dynamics, and hence reflects fundamental properties of the rhythm.

In a preferred embodiment, a first cardiac rhythm electrogram of known origin, preferably of supraventricular origin and most preferably a sinus rhythm, is sensed and a phase space representation or trajectory is generated for use as a template. A second or test cardiac rhythm electrogram is sensed and a phase space representation is generated from the detected waveform complex. This second phase space representation is compared to the template to distinguish between the origins of the first and second cardiac rhythms. If a test trajectory is sufficiently different from the template trajectory, the test complex is deemed to have different dynamics, and therefore be from a different conduction pathway, and hence from a different origin, than the template. For example, ventricular tachycardia can be distinguished from conducted supraventricular rhythms when this formulation is applied to electrograms recorded locally in the ventricle with a normal sinus rhythm serving as the template.

In the preferred embodiment, comparison of the trajectories is accomplished by determining the distance in phase space of each point of the test trajectory to the closest point on the template trajectory. The largest of these shortest distances is used to characterize the similarity of the test trajectory to the template trajectory. The distance between two trajectories is determined in the following way. A lattice or grid is established for the phase space during template formation. For each point in the lattice, the distance, as given by a metric defined for the space, is calculated to each point of the template trajectory. The minimum distance is retained and associated in a memory with the lattice point. When the algorithm is run, each point of the trajectory of the test electrogram specifies a lattice point in the phase space. The distance associated with the lattice point is fetched from memory to provide an approximation of the shortest distance to the template trajectory. The maximum of these distances among all points in the test trajectory serves as the distance between the two trajectories, and hence as a measure of degree of similarity between the dynamics of the two rhythms.

In the preferred embodiment, the metric, or distance measure, used is the square of the Euclidean norm, $$d(\bar{x},\bar{y}) = \sum_{i=1}^{m} (x_i - y_i)^2,$$

where $x_i$ and $Y_i$ are the $i^{th}$ components of the vectors $\bar{x}$ and $\bar{y}$, and m is the dimensionality of the space. Other metrics are possible, such as the $l^\infty$ norm (read "l-infinity"), $$d(\bar{x},\bar{y}) = \max_{i} |x_i - y_i|,$$

or the $l^1$ norm, $$d(\bar{x},\bar{y}) = \sum_{i=1}^{m} |x_i - y_i|.$$

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE PREFERRED EMBODIMENT

Figure 1A:
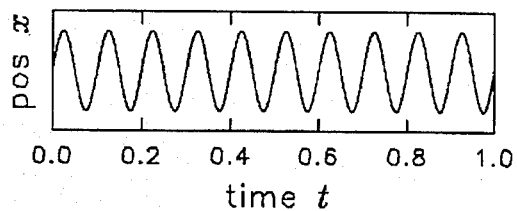
FIGS. 1a–c illustrate the phase space representation of a simple oscillator.
Figure 1B:
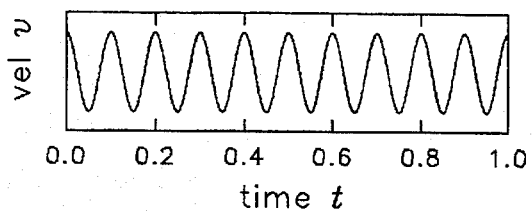
Figure 1C:
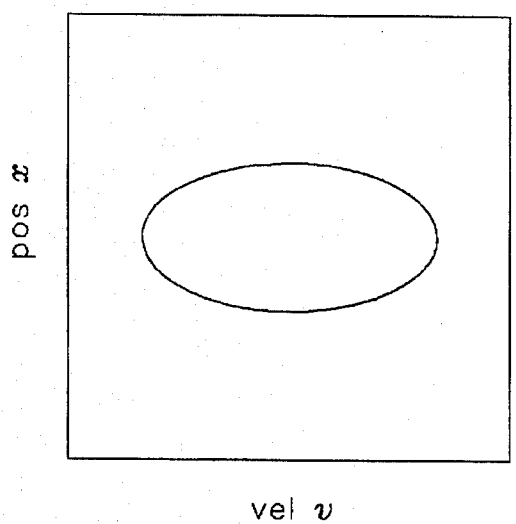

The concepts of phase space representation of a dynamical system are illustrated in FIGS. 1a–c and 2a–c. A simple oscillator has two degrees of freedom: the position and velocity. The dependence of these variables on time is shown in FIGS. 1a and 1b. Plotted against each other in phase space, as shown in FIG. 1c, these variables execute an ellipse. The state of the system moves along the ellipse as the position and velocity oscillate. The ellipse characterizes the dynamics of an oscillator.

Figure 2A:
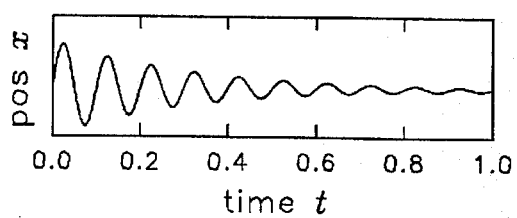
FIGS. 2a–c illustrate the phase space representation of a damped oscillator.
Figure 2B:
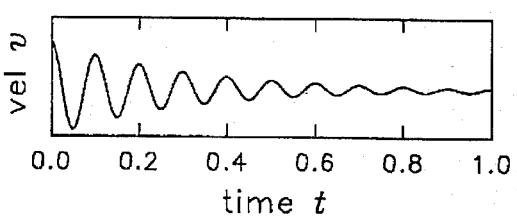
Figure 2C:
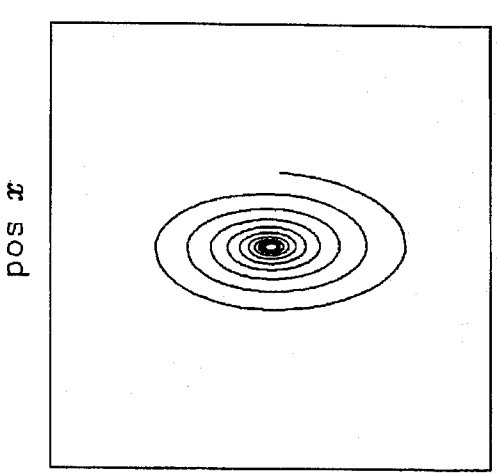

When friction is added to the dynamics, the amplitude of the variables decay with time, as shown FIGS. 2a and 2b for a damped oscillator. The decreasing amplitude causes the trajectory in phase space to spiral to the origin as illustrated in FIG. 2c. The very different behavior of the two systems is thus readily apparent in the phase space representations shown in FIGS. 1c and 2c.

The invention will first be considered with a discussion of the representation of a dynamical system in phase space. A trajectory in an m-dimensional phase space is reconstructed from a sequence of samples $\{x_i\}$ by forming a sequence of vectors $\{\bar{x}_j\} = \{[x_j, x_{j-l}, \ldots, x_{j-(m-1)l}]\}$, where l is the lag. For example, with m=3 and l=2, and with the sequence of samples being $\{x_i\}$, the sequence of vectors would be $x_5, x_3, x_1], x_6, x_4, x_2], x_7, x_5, x_3], \ldots$ In this example, the sequence of vectors would trace out a trajectory in three dimensional space. This simple technique of delay embedding generates a trajectory that is topologically equivalent to that of the true phase space.

As the dimension of phase space used to represent the system increases, the computational demands of the method of the invention increase exponentially. In addition, there is an upper limit to the dimensionality of the space, beyond which no further improvement in discrimination is expected. It has been found that for distinguishing cardiac rhythms a three dimensional space is preferred.

The optimal lag l for delay embedding depends on the details of the data. If l is short relative to the time scale over which the electrogram fluctuates, then the components of the vector will be similar in magnitude, and a trajectory will be executed that falls close to the diagonal. If l is long then the first component of the vector will have returned to zero by the time the second component encounters a QRS complex and begins to climb away from zero. The trajectory will then consist largely of excursions along the axes. The optimal lag is one which spreads the trajectory out in phase space. Theoretical considerations suggest that the first zero crossing $\tau_0$ of the autocorrelation function provides a good lag time. This lag time is 9 msec for the preferred embodiment.

Figure 3:
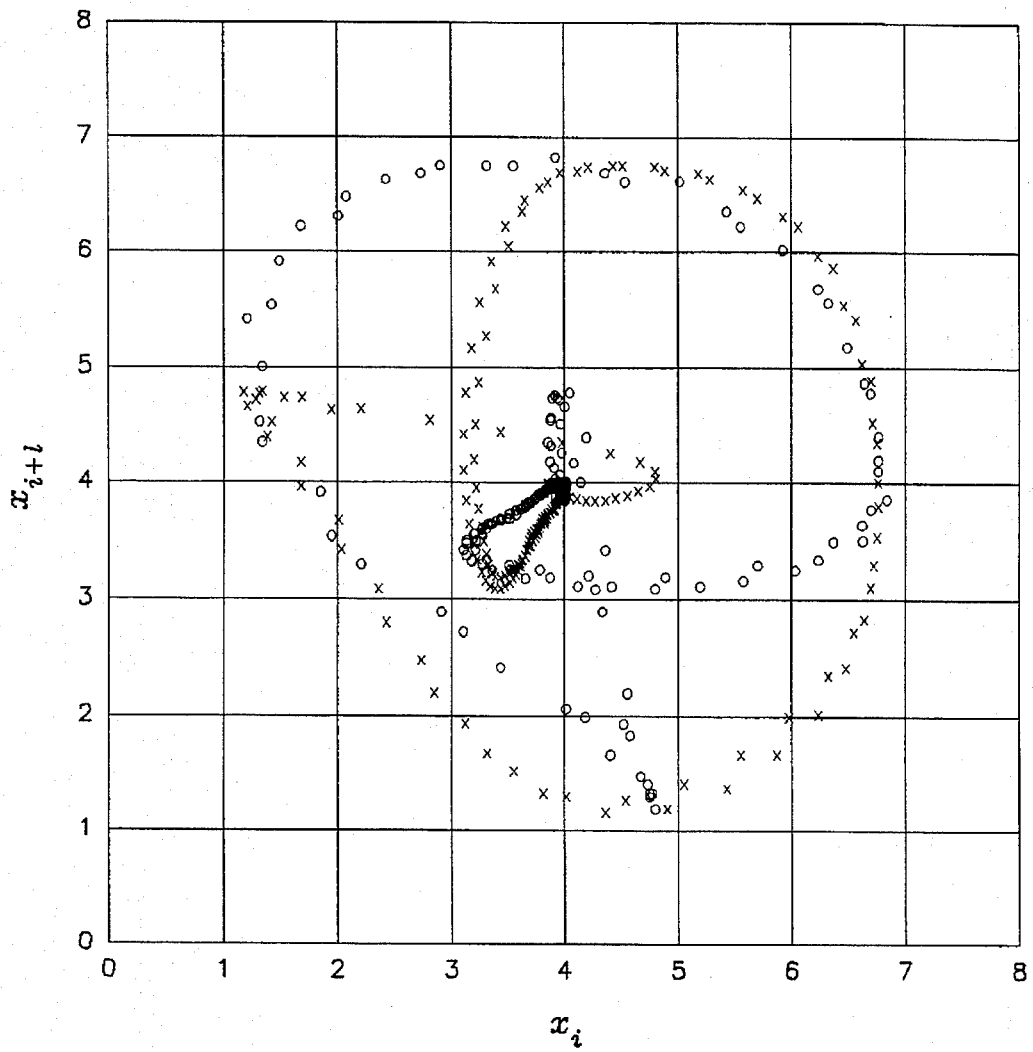
FIG. 3 is a two dimensional plot of the trajectories of two different cardiac rhythms in phase space.

Referring now to FIG. 3, the steps for providing an error measure that reflects the degree of similarity between two trajectories in m-dimensional space will be discussed. The value of the error measure can be used to infer the origin of the cardiac rhythm. This will be discussed in more detail below with reference to FIGS. 4 and 5. A template trajectory is constructed, preferably from an electrogram of a sinus rhythm for a given patient. The trajectories are sets of vectors, represented graphically as sets of points distributed in space. FIG. 3 illustrates a plot for m=2 dimensions. A higher dimension provides better separation between the trajectories and, as mentioned above, m=3 is used in the preferred embodiment. However, m=2 is used here for convenience of illustration. An 8×8 grid is established, creating 64 bins with the centers of the bins providing a lattice of points which are used for the distance calculations. In the figure the symbols 'X' and 'O' represent trajectories from different rhythms. It should be understood that no physical plot or display is required or desired to practice the invention in an ICD. In practice, constructing or creating a trajectory involves storing numbers in a memory.

The template is constructed by first obtaining the set of vectors generated by the template rhythm which is preferably of supraventricular origin, typically a sinus rhythm. One or more QRS complex may be used to generate the template. Because the trajectories do not have time as a variable, the starting point of the trajectory construction is not relevant. The space is partitioned into bins, and the distance from the center of each bin to each point of the template trajectory is calculated. The minimum distance between the center of each bin and the template trajectory is recorded and associated with the bin in memory. Since the dynamics of a given patient's cardiac system may change over time, it may be desirable to replace the template from time to time with a new template, again preferably based on a sinus rhythm.

When the discrimination algorithm is run, a trajectory is executed for each test QRS complex. Each vector in the trajectory will fall in a bin. The minimum distance to the template trajectory, which was calculated for each bin during template generation, is fetched from memory for each vector. The largest of these distances approximates the largest distance from the test trajectory to the template and is returned as the error measure of the test complex relative to the template. This technique requires substantially less computational complexity than would be required to calculate the distance between every point in a test complex and every point in the template. The distance from the center of the bin to the template trajectory is an approximation of the distance from the test vector to the template trajectory. The error in the approximation can be made arbitrarily small by increasing the resolution of the spatial quantization. However, this increases computational complexity and may not be necessary to achieve the desired discrimination capability. It has been found that sufficient resolution is obtained with an 8× 8×8 grid having 512 bins.

If the error measure is sufficiently large, the test complex is deemed to be different from the template rhythm. For example, if a supraventricular rhythm were used in generating the template (e.g., atrial fibrillation or sinus rhythm), then a large error measure would indicate that the test rhythm is of ventricular origin, (e.g., ventricular tachycardia), and appropriate therapy would be delivered.

A great advantage of this algorithm for low-powered devices is that no calculations need to be performed after the template has been formed. The error measure of each complex is obtained by memory accesses and compares.

In order to further reduce the computational requirements of the system of the invention, the discrimination algorithm may be triggered to run only when there is a need to determine whether a rhythm is of ventricular or supraventricular origin. The algorithm may be triggered each time the detected heart rate exceeds a predetermined threshold and/or at such time as other discriminating criteria provide a trigger.

Computational savings are achieved during template formation by effectively neglecting trajectory points near the origin. Since the electrogram voltage is near zero during diastole, bins near the origin of the phase space will contain the vast majority of points, yet these points contain no information about the dynamics of the waveform. For this reason, points near the origin are excluded from the error calculation. Thus, in the preferred embodiment, no calculations are performed for template trajectory points falling in the 8 bins around the phase space origin. Rather, the distances associated with these lattice points are automatically set to zero.

Figure 4:
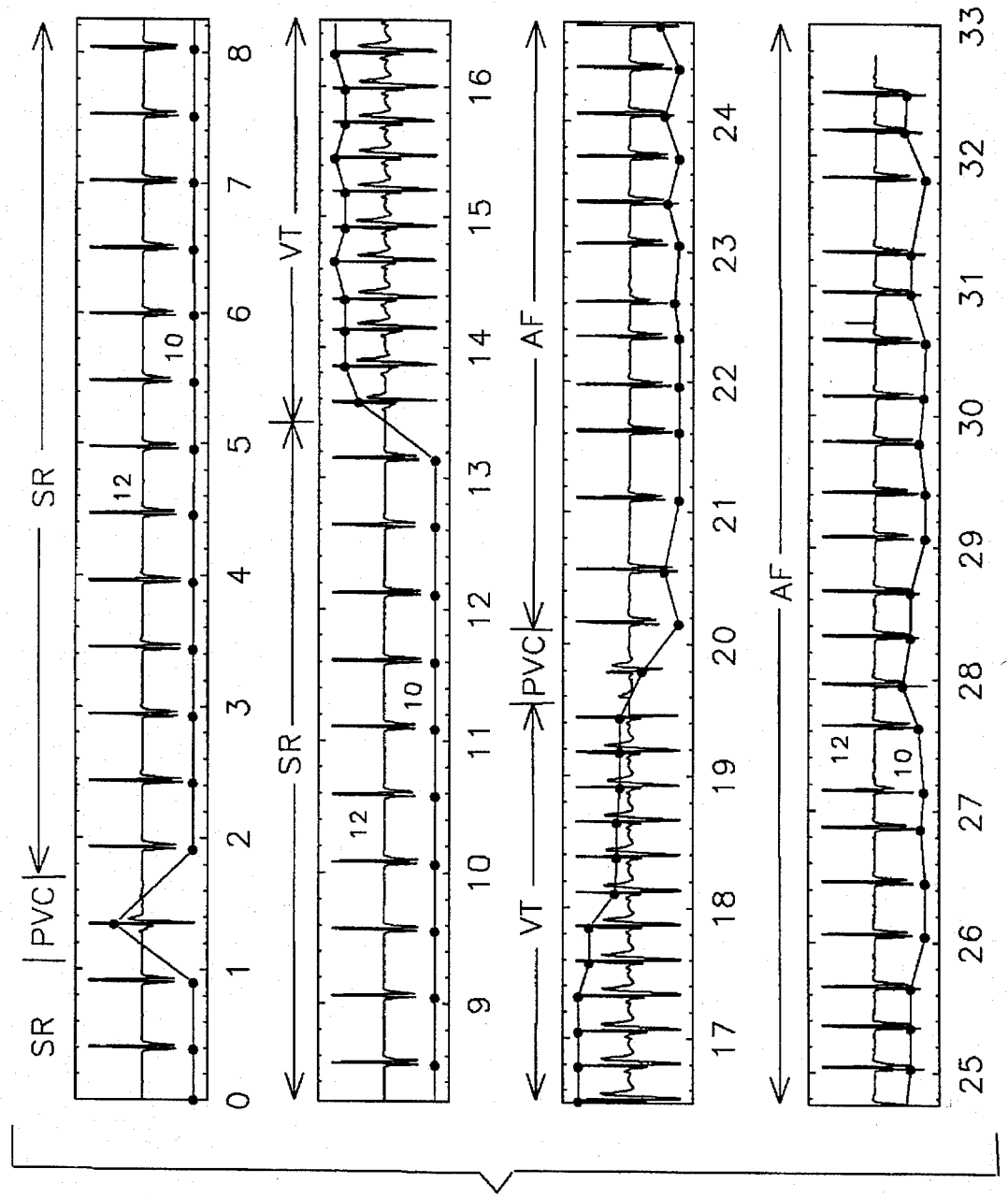
FIG. 4 gives the output of the arrhythmia discrimination algorithm for each QRS complex in stored electrogram.

FIG. 4 presents an example of the output 10 of the discrimination algorithm generated from a stored electrogram 12. The electrogram 12 is annotated above each panel, where SR is sinus rhythm, PVC is premature ventricular contraction, VT is ventricular tachycardia, and AF is atrial fibrillation. These results were obtained using m=3, l=9 msec, and a test-trajectory resolution of N=8 bins per dimension. A Euclidean metric, defined above, was used for distance calculations. The 10 sinus complexes between t=1.8 sec and t=6.6 sec served as the template. For purposes of this example, the complexes used to generate the template are also compared against the template. As expected, the results of these comparisons are close to zero.

Figure 5:
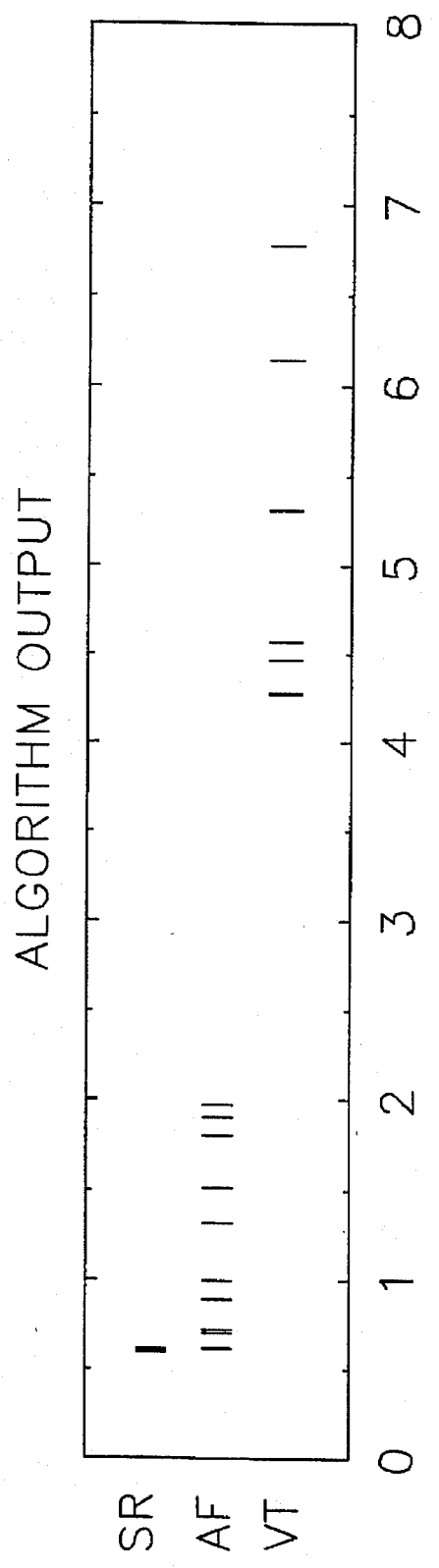
FIG. 5 gives the output of the arrhythmia discrimination algorithm grouped by cardiac rhythm.

The error measure or qualifier output, grouped according to rhythm, is presented in FIG. 5. As shown in this figure, a range of thresholds ($2.0 \leq \theta \leq 4.2$) would successfully distinguish ventricular tachycardia from the supraventricular rhythms.

Figure 6:
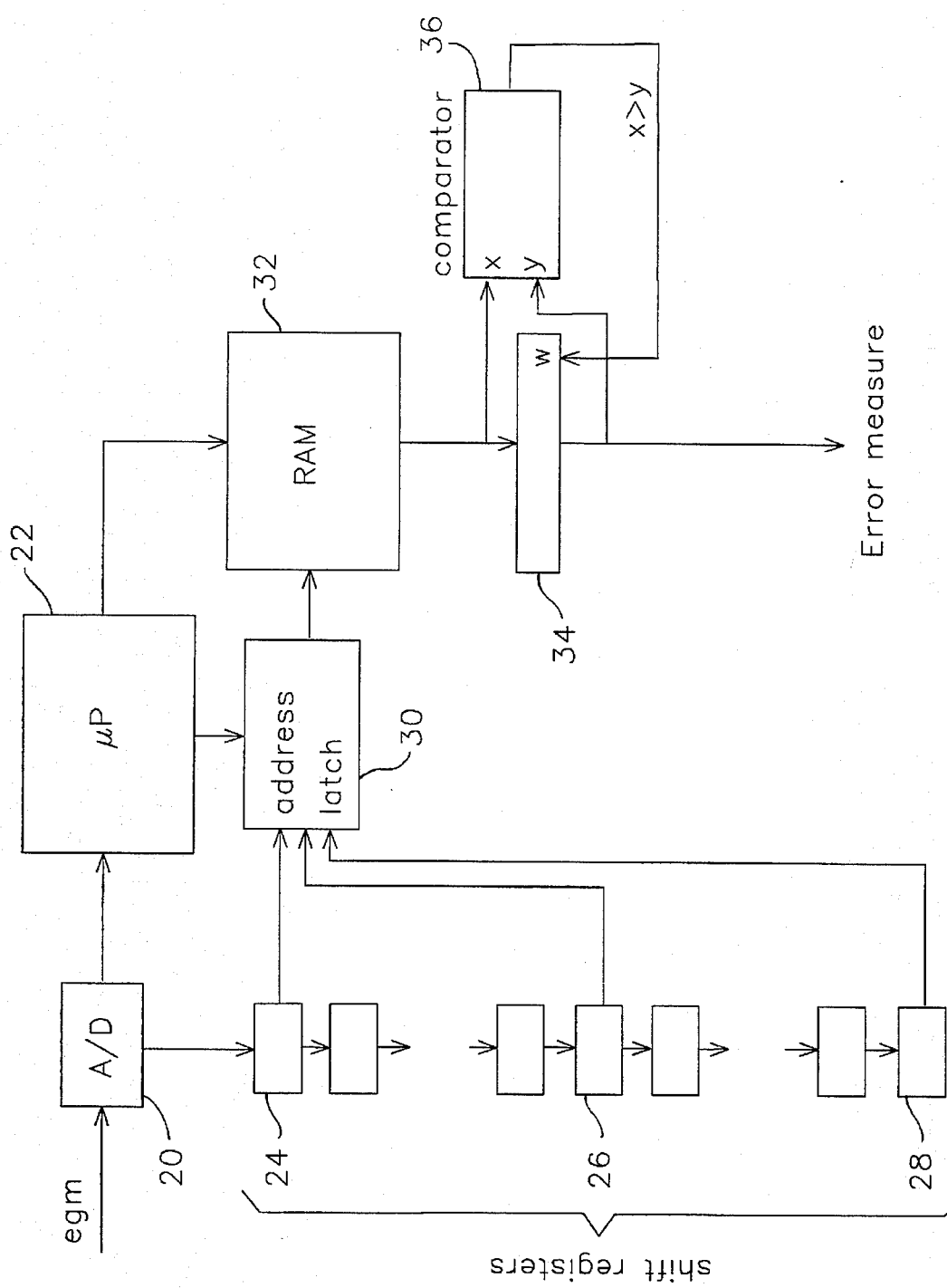
FIG. 6 is a schematic diagram of a hardware implementation of the invention.

The invention may be practiced by implementation in hardware or software or some combination of the two. A hardware implementation of a preferred embodiment of the invention will now be discussed with reference to FIG. 6. An electrogram signal is received from a bipolar ventricular sensor (not shown) by an analog to digital converter 20. The analog to digital converter 20 provides a first output to a microprocessor and related hardware 22 for heart rate analysis and other desired processing. The sampling period is preferably 1 msec but other rates can be used. A second output from analog to digital converter 20 is provided to a string of 19 3-bit shift registers. Since the space is quantized to 8 bins per dimension, the 3 most significant bits of each sample are sufficient to uniquely specify one component of the bin's address. A first shift register 24, a tenth shift register 26 and a last (nineteenth) shift register 28 together provide the address containing the distance associated with the corresponding lattice point. The address is latched in an address latch 30 and presented to a random access memory (RAM) 32 which contains the shortest distance from each of the 512 bins to the template trajectory. When a memory location in RAM 32 is accessed, it provides an output to output register 34. This output from RAM 32 is also provided to a comparator 36. Comparator 36 determines whether the output from RAM 32 is greater than the value currently stored in register 34. If the new value is larger, the output of comparator 36 enables the write function of register 34 to write the new value from RAM 32 over the old value in register 34. In this way, the largest of the minimum distances from the test trajectory to the template trajectory is determined. The output is the error measure for each QRS complex which may be used by microprocessor 22 to determine the appropriate therapy. In addition, these error measures may be recorded in memory linked to a stored electrogram to assist a physician in later diagnosis.

Figure 7:
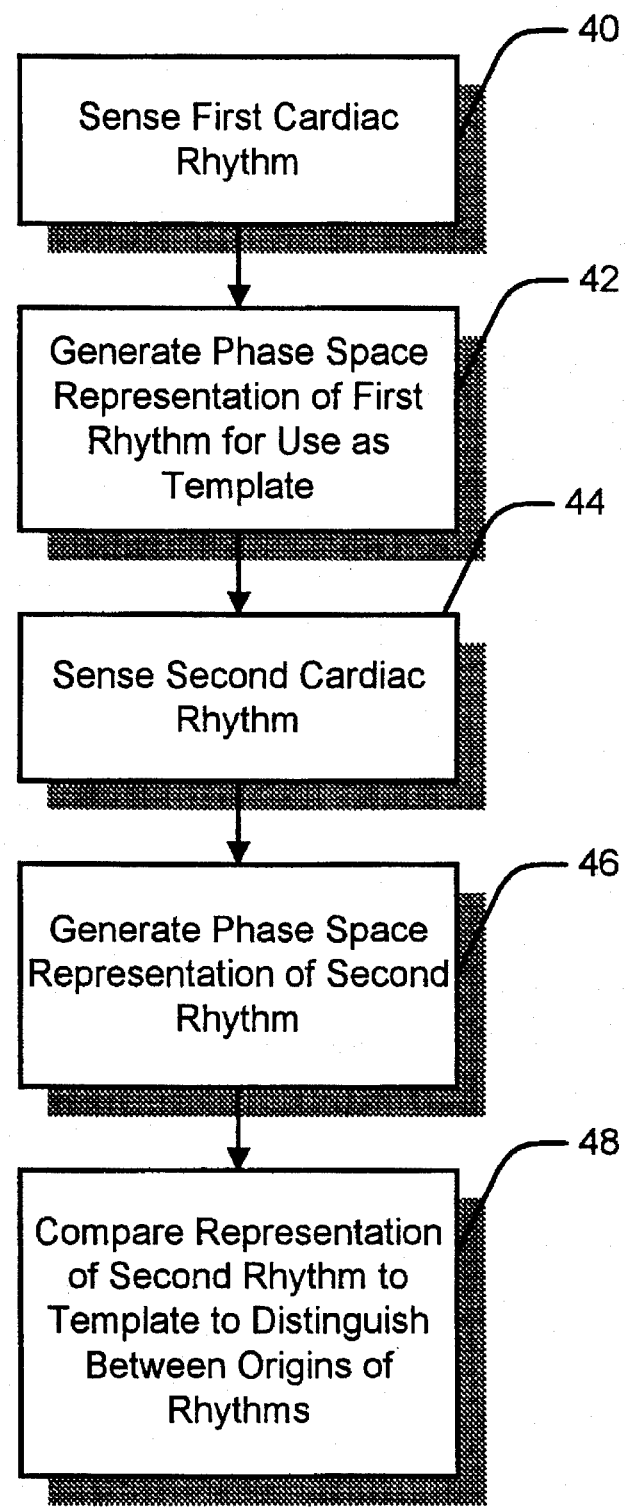
FIG. 7 is a flow chart illustrating the method of the invention.

The general method steps of the invention will now be discussed with reference to FIG. 7. A first cardiac rhythm is sensed for use in generating a template at step 40. As discussed above, this is preferably a sinus rhythm. A phase space representation of this rhythm is generated to provide a template at step 42. This template may be updated from time to time if desired. When the discrimination algorithm is run, a second cardiac rhythm is sensed, preferably in the form of a test QRS complex at step 44. A trajectory in phase space is generated as a representation of this second rhythm at step 46. The test trajectory is compared to the template and the results of this comparison are used distinguish between the origins of the two rhythms at step 48.

The invention has been described with reference to a preferred embodiment of an implantable defibrillator which senses a ventricular intracardiac electrogram. However, other electrogram signals may be used as long as the voltage they sense includes signals from the ventricles. For example, a far field signal sensed between a defibrillation electrode in the right ventricle and the defibrillator housing could be used as could a surface electrocardiogram signal sensed from electrodes placed, for example, on a patient's chest. The invention can be used with external cardiac monitoring equipment as well as implanted devices such as an ICD.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A method for distinguishing between cardiac rhythms having different origins comprising the steps of:
   sensing a first cardiac rhythm;
   generating a phase space representation of the dynamical behavior of said first cardiac rhythm for use as a template;
   sensing a second cardiac rhythm;
   generating a phase space representation of the dynamical behavior of said second cardiac rhythm; and
   comparing the representation of said second cardiac rhythm to said template to distinguish between the origins of said first and second cardiac rhythms.

2. The method of claim 1 wherein said steps of generating a phase space representation include the steps of constructing as a trajectory in m-dimensional space a sequence of vectors generated from the amplitude of m data points of an electrogram of said cardiac rhythm each separated by a lag l from a closest corresponding data point where $m \geq 2$.

3. The method of claim 1 wherein said phase space representations are generated by constructing a trajectory in an m-dimensional phase space from a sequence of samples $\{x_i\}$ provided as amplitude data points of an electrogram by forming a sequence of vectors $\{\bar{x}_j\} = \{[x_j, x_{j-l}, \ldots, x_{j-(m-1)l}]\}$, where l is the lag time and where $m \geq 2$.

4. The method of claim 1 wherein said step of comparing includes the steps of:
   determining a measure of a distance in phase space of each point of said phase space representation of said second cardiac rhythm to a closest point of said template; and
   determining a largest of said measures to provide a value representing a similarity between said first and second cardiac rhythms.

5. The method of claim 4 wherein said step of determining a measure includes determining a square of a Euclidean norm in phase space.

6. The method of claim 4 wherein said step of determining a measure of a distance includes the steps of:
   partitioning said phase space into a grid of m-dimensional bins;
   determining a measure of a shortest distance of each bin to a closest point of said template and storing such measure for each bin in a memory; and
   determining for each point of said phase space representation of said second cardiac rhythm the bin into which it falls and fetching from said memory the measure of said shortest distance for said bin.

7. The method of claim 6 wherein said step of determining a measure includes determining a square of a Euclidean norm in phase space.

8. The method of claim 4 and further including the step of setting a threshold value for distinguishing between a supraventricular and a ventricular cardiac rhythm and comparing said largest measure to said threshold value.

9. The method of claim 1 wherein said step of sensing a first cardiac rhythm includes sensing a rhythm of supraventricular origin.

10. The method of claim 1 wherein said steps of sensing said first and second cardiac rhythms comprise sensing a local electrogram from a single location in a patient's heart.

11. A method for distinguishing between a cardiac rhythm of ventricular origin and a cardiac rhythm of supraventricular origin comprising the steps of:
   sensing a first electrogram comprising a supraventricular origin cardiac rhythm;
   creating a trajectory of said first electrogram in phase space for use as a template representative of a rhythm of supraventricular origin;
   sensing a second electrogram of unknown cardiac origin;
   creating a trajectory of said second electrogram in phase space; and
   comparing the trajectory of said second electrogram to said template to distinguish between the origins of said first and second electrograms.

12. The method of claim 11 further including the step of determining a possible presence of an arrhythmia by continuously sensing an electrogram and analyzing said electrogram for a rapid rhythm prior to creating said trajectory of said second electrogram.

13. The method of claim 11 wherein said steps of creating a trajectory include the steps of creating as a trajectory in m-dimensional space a sequence of vectors generated from the amplitude of m data points of an electrogram of said cardiac rhythm each separated by a lag l from a closest corresponding data point where $m \geq 2$.

14. The method of claim 11 wherein said step of comparing includes the steps of:
   determining a measure of a distance in phase space of each point of said trajectory of said second electrogram to a closest point of said template; and
   determining a largest of said measures to provide a value representing a similarity between said first and second electrograms.

15. The method of claim 14 wherein said step of determining a measure includes determining a square of a Euclidean norm in phase space.

16. The method of claim 14 and further including the step of setting a threshold value for distinguishing between a supraventricular and a ventricular cardiac rhythm and comparing said largest measure to said threshold value.

17. The method of claim 11 and further including the steps of generating a lattice in phase space when said template is created and calculating a shortest distance measure between each lattice point and said template and storing each of said shortest distance measures in a memory and wherein said step of comparing includes determining the closest lattice point in phase space to each point of the trajectory of said second electrogram and looking up said shortest distance measure in said memory for said lattice point to provide a measure of the shortest distance between each point in said trajectory of said second electrogram and said template.

18. The method of claim 17 and further including the step of setting to zero those of said shortest distance measures representative of a diastole portion of said first electrogram.

19. A system for distinguishing between cardiac rhythms having different origins comprising:
   a sensor for sensing cardiac electrograms;
   a first logic circuit coupled to said sensor for generating phase space representations of the dynamical behavior of said sensed electrograms;
   a memory coupled to said first logic circuit for storing a phase space representation of a first electrogram for use as a template; and
   a second logic circuit for comparing a representation of a first electrogram to a representation of a second electrogram to distinguish between the origins of said first and second electrograms.

20. The system of claim 19 wherein said first logic circuit includes an analog to digital converter coupled to said sensor to receive an analog electrogram input and provide a digitized electrogram output.

21. The system of claim 20 wherein said first logic circuit further includes a string of shift registers coupled to receive said digitized electrogram output from said analog to digital converter and an address latch coupled to at least two of said shift registers to provide a sequence of vectors comprising said phase space representations.

22. A system for distinguishing between cardiac rhythms of ventricular origin and cardiac rhythms of supraventricular origin comprising:

a sensor cardiac electrograms;

an analog to digital converter coupled to said sensor for providing digitized electrogram outputs;

a processor coupled to said analog to digital converter for generating phase space representations of the dynamical behavior of said digitized electrogram outputs;

a memory coupled to said processor for storing a phase space representation of a first electrogram for use as a template; and wherein said processor compares the representation of a second electrogram output to said template to distinguish between the origins of said first and second electrogram outputs.

23. The system of claim 22 wherein said processor includes a string of shift registers coupled to receive said digitized electrogram output from said analog to digital converter and provide a sequence of vectors comprising said phase space representations.

* * * * *